United States Patent [19]

Smith et al.

[11] 4,128,501
[45] Dec. 5, 1978

[54] PROCESS FOR THE PREPARATION OF ORGANO-MAGNESIUM COMPLEXES

[75] Inventors: William N. Smith, Quaker Town, Pa.; Dennis B. Malpass, LaPorte; Joseph H. Merkley, Dayton, both of Tex.

[73] Assignee: Texas Alkyls, Inc., Deer Park, Tex.

[21] Appl. No.: 809,750

[22] Filed: Jun. 24, 1977

[51] Int. Cl.$^2$ .................................................. C08F 4/50
[52] U.S. Cl. ............................. 252/431 R; 252/429 C
[58] Field of Search ............ 252/431 R, 429 C, 429 B

[56] References Cited

U.S. PATENT DOCUMENTS 3,737,393  6/1973  de Vries ........................... 252/431 R

OTHER PUBLICATIONS

Malpass et al., J. Organometal. Chem. 93, (1975) pp. 1-8.

Primary Examiner—Patrick Garvin
Attorney, Agent, or Firm—Edwin H. Baker

[57] ABSTRACT

Hydrocarbon soluble organo-magnesium complex of the formula $$(RR'Mg)_m \cdot (R_3Al)_n$$

wherein R is a primary, secondary or tertiary alkyl group having from 1 to 25 carbon atoms. R' is a primary alkyl group having 1 to 25 carbon atoms, or phenyl group, or mixture thereof, and m and n are numbers such that the ratio of $m/n$ is about one or greater.

These complexes are prepared by reacting magnesium metal with a primary alkyl halide or phenyl halide in the presence of a hydrocarbon solvent and adding thereto a metal organo-aluminate of the formula $R_4AlM$ wherein R is as defined and M is sodium, potassium or lithium. The metal organo-aluminate compound functions as a solubilizing agent for organo-magnesium compounds which are normally only slightly soluble in hydrocarbon media. These complexes are characterized by very low halide content, lack of ether contamination, magnesium to aluminum ratios of between about 1:2 to about 20:1, and hydrocarbon solubility.

4 Claims, No Drawings

PROCESS FOR THE PREPARATION OF ORGANO-MAGNESIUM COMPLEXES

BACKGROUND OF THE INVENTION

Dialkylmagnesium compounds are well known in the art. However, the production of soluble dialkylmagnesium compounds, free of solvation and chloride, by the direct reaction of magnesium with a halide, has heretofore been accomplished only recently.

U.S. Pat. No. 3,737,393 teaches hydrocarbon soluble alkyl magnesium-alkyl aluminum complexes prepared by interaction of certain organo-aluminum compounds with the reaction product of magnesium and certain alkyl halides.

Various organo-aluminum - organo-magnesium complexes have been prepared by reaction of a trialkylaluminum compound with a desolvated (ether-free) Grignard reagent, by electrolysis of mixtures of alkali metal tetraalkylaluminates using a magnesium anode, and by the reaction of dialkylmagnesium compounds, prepared via the mercury-magnesium exchange method, with trialkylaluminum compounds. The complexes prepared by these processes have low Mg/Al ratios, in the range of 0.5 to 1.0 depending upon the stoichiometry of starting materials.

The electrolysis method requires the use of mixed $R_4AlM$ compounds (M=alkali metal) in a molten state and the preferred temperature range in 100°–125° C. See for example, U.S. Pat. No. 3,028,319. This temperature range precludes the preparation of complexes which may be easily pyrolyzed, for example, when R=isobutyl. Furthermore, complexes with Mg/Al ratios greater than 0.5 are not produced by this procedure.

It is an object of the present invention to prepare hydrocarbon soluble organo-magnesium complexes, including those complexes containing the normally insoluble lower dialkylmagnesium compounds suitable for use as co-catalysts for the polymerization of olefins, diolefines, or olefin oxides.

It is another object of the present invention to prepare organo-magnesium complexes wherein the Mg/Al ratio is about one or greater. Other objects of the present invention will become apparent from the description contained below.

DETAILED DESCRIPTION OF THE INVENTION

The present invention relates to a hydrocarbon soluble organo-magnesium complexes of the formula $$(RR'Mg)_m \cdot (R_3Al)_n$$

wherein R is a primary, secondary, or tertiary alkyl group having from 1 to 25 carbon atoms, preferably having 1 to 8 carbon atoms, most preferably ethyl, or isobutyl. R' is a primary alkyl group having 1 to 25 carbon atoms, preferably 1 to 10 carbon atoms or phenyl group, or mixture thereof, more preferably a primary alkyl having 1 to 4 carbon atoms, and m and n are numbers such that the ratio of m/n is about one or greater, preferably between about 1 to 10. As an illustration, R can be methyl, ethyl, n-propyl, isopropyl, n-butyl, isobutyl, sec.-butyl or t-butyl. R' can be methyl, ethyl, n-propyl, n-butyl, or n-amyl and to a process for its preparation.

These organo-magnesium complexes are prepared by (1) reacting magnesium metal with a primary alkyl halide or phenyl halide in the presence of a hydrocarbon solvent and (2) adding thereto a metal organo-aluminate compound of the formula $R_4AlM$ wherein R is as defined and M is sodium, potassium or lithium, preferably after the completion of the reaction.

Illustrative of these organo-magnesium compounds are the following: dimethylmagnesium, diethylmagnesium, di-n-propylmagnesium, di-n-butylmagnesium, di-n-amylmagnesium, di-n-hexylmagnesium, diphenylmagnesium, and the like. The preferred compounds are dimethylmagnesium, diethylmagnesium, di-n-butylmagnesium and di-n-amylmagnesium. Particularly preferred are the primary alkyl magnesium compounds wherein the alkyl group is n-butyl and n-amyl.

The organo-magnesium moiety in the complexes of the present invention is generally derived from bis primary dialkyl-or diphenylmagnesium compounds, obtained via the direct reaction of magnesium with a primary alkyl or phenyl halide in a hydrocarbon solvent. Preferably the alkyl halide is not methyl chloride or ethyl chloride.

Although magnesium turnings or shavings of commercial grade that have been further activated by milling or any other of the known methods for activating magnesium can be used in the processes herein described for the preparation of organo-magnesium complexes, it is preferable to use magnesium in a finely divided state, for instance, as a powder with a particle size less than 100 $\mu$. With such fine particle size it is unnecessary to activate the metal.

Although the Applicants do not wish to be held to a particular theory of the reaction mechanism, it is thought that the first reaction proceeds through a Grignard type intermediate $(R'MgX)_m$ which, in the absence of a solvating species, disproportionates via the Schlenk equilibrium to the organo-magnesium and magnesium halide as follows

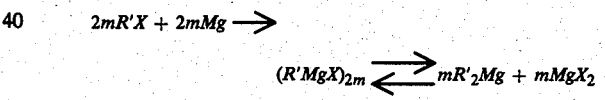

wherein R' is as defined, X is chlorine, bromine or iodine, preferably chorine, and m is an integer.

The extent of the disproportionation is dependent upon the nature of the solvent, the nature of the alkyl group and the particular halide involved.

As stated previously, the complexes of the present invention are prepared by initially reacting magnesium metal with a halide of the formula $$R'X$$

wherein R' is as defined above and X is chlorine, bromine or iodine, preferably chlorine, and subsequently adding the metal organo-aluminate compound directly to the reaction product, either during or after the reaction.

The magnesium and the halide are normally reacted in a molar ratio of 1.2 to 1.0, i.e., a 20% molar excess of magnesium. It is understood, however, that the ratio of reactants can be varied in the range from about 1 to 2 moles of magnesium per mole of halide, and preferably in the range from about 1.1 to 1.3, i.e., a 10–30% excess magnesium. This excess magnesium is desirable to minimize Wintz coupling reactions.

Although the reaction of the halide with magnesium can be conducted in the absence of a solvent wherein an excess of the alkyl or phenyl halide serves as the dispersion medium, it is preferable that the reaction of the magnesium with the halide be conducted in a hydrocarbon solvent.

The term hydrocarbon solvent, as used herein, is used to designate any inert aliphatic and aromatic hydrocarbon. Illustrative of the hydrocarbons which can be used in the present invention are the following: isopentane, n-hexane, n-heptane, n-octane, cyclohexane, methylcyclohexane, benzene, and toluene and halogenated aliphatic cycloaliphatic hydrocarbons such as chlorobenzene. Particularly preferred solvents are those aliphatic and aromatic hydrocarbons which boil between 69° and 110° C. Particularly preferred aliphatic and cycloaliphatic hydrocarbons are those having 5 to 20 carbon atoms especially alkyl, cycloalkyl, aryl and alkaryl hydrocarbons having from 6 to 15 carbon atoms. The most preferred solvents are n-heptane, cyclohexane and benzene. The hydrocarbon solvent is normally employed in amounts from about 10 to 20 times the weight of magnesium charged.

The reaction between the metallic magnesium and the alkyl or phenyl halide can be carried out at a temperature between about 20° C. and about 200° C., preferably between about 60° C. and about 100° C. This reaction must be carried out in the absence of oxygen. Thus, the reaction can be carried out under an atmosphere of an inert gas such as nitrogen or argon. The pressure is not critical and may vary between wide limits, but should be at least high enough to ensure that the reaction medium and the alkyl or aryl halide are substantially in a liquid state. It has also been found desirable to vigorously stir the reaction mixture.

Although the Applicants do not want to be restricted to a particular theory, they believe that the added metal alkyl aluminate reacts with the magnesium halide reaction product according to the following

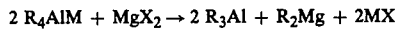

$$2\ R_4AlM + MgX_2 \rightarrow 2\ R_3Al + R_2Mg + 2MX$$

The $R_3Al$ and $R_2Mg$ reaction products of this second reation are believed to interact with the organo-magnesium compound reaction product, i.e., $R'_2Mg$, to form complexes of the formula:

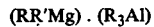

$$(RR'Mg) \cdot (R_3Al)$$

The RR'Mg moiety is used to designate the combination of $R_2Mg$ and $R'_2Mg$ where R and R' are as defined. The R and R' groups are not bonded to a specific magnesium atom but associate from one magnesium atom to another.

The metal alkyl aluminates of this invention have the general formula $R_4AlM$ in which R is a primary, secondary, or tertiary alkyl group having from 1 to 25 carbon atoms, preferably from 1 to 10 carbon atoms and most preferably ethyl or isobutyl, and M is sodium, potassium or lithium.

Examples of the alkyl groups of the above formula include methyl, ethyl, n-propyl, isopropyl, n-butyl, isobutyl, sec.-butyl, t-butyl, the pentyls, the hexyls, the heptyls, the octyls and up to hexacosyls.

Illustrative of the alkyl metal aluminates are the following: tetramethyl sodium aluminate, tetraethyl sodium aluminate, tetrapropyl sodium aluminate, tetraisobutyl sodium aluminate, tetraoctyl sodium aluminate, tetramethyl potassium aluminate, tetraalkyl potassium aluminate, tetrapropyl potassium aluminate, tetraisobutyl potassium aluminate, tetraoctyl potassium aluminate, tetramethyl lithium aluminate, tetraethyl lithium aluminate, tetrapropyl lithium aluminate, tetraisobutyl lithium aluminate and tetraoctyl lithium aluminate.

The amount of metal alkyl aluminate that is added to the reaction product of the magnesium and the alkyl or phenyl halide is between about 0.05 and 2.0 mole per mole of organo-magnesium compound to be solubilized.

When the alkyl metal aluminate compound is employed in amounts greater than 1:1 with the organo-magnesium compound (Mg/Al ratio is less than one) then sodium, potassium or lithium metal from the metal alkyl aluminate will be present in solution.

Preferably the amount is between about 0.10 and 1.0 mole per mole. More preferably the amount is between about 0.15 and 0.50 mole per mole.

The optimum quantity of the metal alkyl aluminate used depends upon the nature of the metal and alkyl group of the metal alkyl aluminate, the particular alkyl or phenyl halide reactant and the particular hydrocarbon dispersion medium used, but can be easily determined by routine experimentation, well within the skill of those in the art.

The addition of the alkyl metal aluminate and subsequent steps must be carried out in the absence of oxygen. Thus, the addition and subsequent steps must be under an inert atmosphere of a gas such as nitrogen or argon.

In the practice of the process of the present invention, recoveries of about 60–80% of the theoretical amount of organo-magnesium can be achieved. The remaining portion of the original starting materials is presumably lost to thermal decomposition and coupling.

The solubilization of the organo-magnesium compound proceeds well at room temperature and is normally completed in two-three hours. However, to facilitate solubilization, the reaction mixture can be heated during the solubilization. The upper temperature limit for this step is dependent upon the decomposition temperature of the particular alkyl metal aluminate used, the decomposition temperature of the dialkyl magnesium compounds and the boiling point of hydrocarbon solvent in the absence of any applied pressure. During the addition of the aluminate, it is desirable to vigorously stir the reaction mixture.

The alkyl metal aluminate can be added to the reaction mixture of the magnesium and alkyl or phenyl halide either during or after the completion of the reaction or at both times.

Preferably the aluminate is added as a solution in a hydrocarbon as previously defined with vigorous stirring.

The reactant mixture obtained after the addition of the alkyl metal aluminate compound is normally filtered and the solid washed with several portions of the hydrocarbon solvent used. The resultant wash solution can then be added to the filtrate.

After filtration of the reaction mixture, the resulting solution contains the organo-magnesium complexes of the present invention and can then be diluted or concentrated as desired. The complexes can be isolated by evaporating the solvent to yield the viscous liquid or solid complex. However, it is preferred to handle these complexes in solution.

It is apparent to one skilled in the art that the complexes of the present invention are a mixture of complexes having different values for m and n and that the m/n value as used herein is an average value for these numbers. It is not necessary, or even desirable, to isolate individual complexes, however, since the mixtures work just as well as the individual complexes. Furthermore, it is recognized that a certain degree of alkyl group transfer occurs between the aluminum and magnesium atoms of the complex. Thus, the formulae given for the complexes of the present invention are empirical rather than exact.

The complexes of the present invention are characterized by a high Mg/Al ratio. They are further characterized by their freedom from undesirable contamination by halides. Furthermore, since the method of forming the complexes of the present invention does not require the use of an ether catalyst, the final product is completely ether-free.

Those compounds of the present invention which have sufficiently high Mg/Al ratios (m/n of 4 or greater) can be useful in situations where organo-magnesium reagents are desired, i.e., the complexes can be used to simulate the "pure" organo-magnesium reagent in reactivity, since they can contain 80 mole percent or greater $R'_2Mg$. In this regard, the complexes of the present invention have the substantial advantage in that they are highly soluble in hydrocarbon solvents, whereas the pure organo-magnesium reagents are, in general, insoluble. Since these complexes are completely free of ether contamination, they can be used as Ziegler type catalysts without catalyst poisoning which may result from the ether contamination. Organo-magnesium compounds are effective catalysts for the polymerization of ethylene or propylene in the presence of titanium tetrachloride and, for the polymerization of 1,3-butadiene or 2-methyl-1,3-butadiene in the presence of titanium tetraiodide.

The present invention will be further illustrated by the following examples.

EXAMPLE I

To a 300 milliliter three neck flask equipped with a magnetic stirrer, reflux condenser, and addition funnel were added 7.7 grams (0.317 gram-atom) of magnesium powder (100 mesh) and 1.77 grams (0.019 mole) n-butyl chloride and a few crystals of iodine. All equipment was previously flushed while hot with dry nitrogen and all reactions and manipulations carried out under a nitrogen blanket. The mixture was heated to 95° C. and the reaction initiated. Then 80 milliliters of heptane (previously dried over 4A molecular sieves) was charged to reaction mixture. Finally, 26.1 grams (0.282 mole) n-butyl chloride was charged by the addition funnel at a rate to maintain a gentle reflux after the addition of the n-butyl chloride. During the addition, the reaction mixture became very viscous and had a paste-like consistency. The mixture was allowed to cool to 30° C. Analysis showed the presence of no metal alkyl to be in solution.

EXAMPLE II

To a reaction mixture of di-n-butylmagnesium prepared as described in Example I was added 22 milliliters of a 1.03M solution (0.0226 mole) of sodium tetraethylaluminate. The aluminate was prepared by the addition of 83 grams (0.727 mole) of triethylaluminum to 16 grams of sodium dispersion in 200 milliliters of benzene at 60° C. The di-n-butylmagnesium reaction mixture immediately became thinner and was heated to 80° C. for one hour after the addition of the sodium tetraethylaluminate. The mixture was then allowed to cool to 40° C., filtered and washed with 100 milliliters of heptane.

The filtrate (143.6 grams) contained 2.55 grams magnesium or 0.105 mole of dialkylmagnesium (0.094 mole di-n-butylmagnesium and 0.011 mole diethylmagnesium) as a 9.62 percent by weight solution of dialkylmagnesium (70% of theory). The filtrate also contained 0.61 grams of aluminum or 0.0226 mole of triethylaluminum, as 1.80 percent by weight solution, yielding a magnesium to aluminum ratio of 4.64. No sodium was detected in product.

EXAMPLE III

To a reaction mixture of di-n-butylmagnesium prepared as described in Example I was added 50 milliliters (0.03 mole) of a sodium tetraisobutylaluminate slurry. The aluminate was prepared by the addition of 51 milliliters (0.20 mole) of triisobutylaluminum to 12 grams of sodium dispersion in 100 milliliters of heptane. The reaction mixture became thinner and was heated at 80° C. for one hour after the addition of the sodium tetraisobutylaluminate. The mixture was then allowed to cool to 30° C., filtered and washed with 30 milliliters of heptane.

The filtrate (85.3 grams) contained 0.87 grams of magnesium or 0.036 mole of dialkylmagnesium (24% of theory) as a 5.8 percent by weight solution. The filtrate also contained 0.36 grams aluminum or 0.013 mole of triisobutylaluminum, as a 3.0 percent by weight solution, yielding a magnesium to aluminum ratio of 2.69. (The low yield of dialkylmagnesium is attributed to the low solubilizing ability of the isobutylaluminum grouping, i.e., use of a larger amount of $NaAlisoBu_4$ would have resulted in a higher yield of $R_2Mg$ solubilized.)

We claim:

1. A process for the preparation of hydrocarbon soluble organo-magnesium complex of the formula

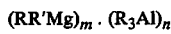

$(RR'Mg)_m \cdot (R_3Al)_n$ wherein R is a primary, secondary, or tertiary alkyl group having from 1 to 25 carbon atoms, R' is a primary alkyl group having 1 to 25 carbon atoms, or phenyl group, or mixture thereof, and m and n are numbers such that the ratio of m/n is about one or greater comprising:
    (a) reacting magnesium metal with primary alkyl halide or phenyl halide of the formula R'X wherein R' is as defined and X is chlorine, bromine or iodine at a temperature between about 20° C. and about 200° C., said magnesium being present in an amount from 1 to 2 moles of magnesium per mole of halide; and
    (b) adding thereto a metal organo-aluminate compound of the formula $R_4AlM$ wherein R is as defined and M is sodium, potassium or lithium in less than a 1:1 mole ratio with the magnesium reaction compounds of step a).

2. The process of claim 1 wherein step a) is conducted in the presence of a hydrocarbon solvent.

3. The process of claim 1 wherein step a) is conducted at a temperature between about 60° C. to about 100° C.

4. The process of claim 2 wherein said hydrocarbon solvent is an alkyl, cycloalkyl, aryl or alkaryl hydrocarbon having 6 to 15 carbon atoms.

* * * * *